United States Patent
Subramanian et al.

(10) Patent No.: US 7,094,928 B2
(45) Date of Patent: Aug. 22, 2006

(54) PROCESS FOR THE SYNTHESIS OF (±) 2-AMINO-N-[2,(2,5-DIMETHOXY PHENYL)-2-HYDROXYETHYL] ACETAMIDE MONOHYDROCHLORIDE

(75) Inventors: Rajaram Sankara Subramanian, Tamil Nadu (IN); Venkatanathan Satagopan, Tamil Nadu (IN); Rajagopalan Srinivasan, Tamil Nadu (IN)

(73) Assignee: Sanmar Specialty Chemicals Ltd., Tamil Nadu (IN)

( * ) Notice: Subject to any disclaimer, the term of this patent is extended or adjusted under 35 U.S.C. 154(b) by 14 days.

(21) Appl. No.: 10/486,230

(22) PCT Filed: Aug. 21, 2002

(86) PCT No.: PCT/IN02/00170

§ 371 (c)(1),
(2), (4) Date: Feb. 6, 2004

(87) PCT Pub. No.: WO2004/018409

PCT Pub. Date: Mar. 4, 2004

(65) Prior Publication Data

US 2004/0198836 A1   Oct. 7, 2004

(51) Int. Cl.
*C07C 233/05* (2006.01)

(52) U.S. Cl. ............ 564/194; 564/196; 564/394; 562/10

(58) Field of Classification Search ........... 564/194, 564/196, 394; 552/10; 562/10
See application file for complete search history.

(56) References Cited

U.S. PATENT DOCUMENTS 6,201,153 B1   3/2001   Ray et al. ............ 564/196

FOREIGN PATENT DOCUMENTS

DE   25 23 735 A1   2/1976
DE   25 06 110 A1   8/1976

OTHER PUBLICATIONS

Meng et al, Zhongguo Yiyao Gongye Zazhi, 2002, 33(5), 213-215. (English abstract also attached, pp. 13-15).*

* cited by examiner

Primary Examiner—Shailendra Kumar
(74) Attorney, Agent, or Firm—Ladas & Parry LLP

(57) ABSTRACT

This invention relates to an improved process for synthesizing (±)-2-Amino-N-[2-(2,5-dimethoxyphenyl]-2-hydroxyethyl acetamide monohydrochloride in good yield and in a cost effective manner from 1-(2,5-dimethoxyphenyl)-2-bromoethanone by reacting the same with hexamine in the presence of novel solvent system comprising Tetrahydrofuran and water. The resulting aminoethanone is acylated with haloacetylchloride and sodium acetate in acetone-water solvent system. This product is reduced selectively first with sodium borohydride and subsequently with stannous chloride. This product is converted in situ to the corresponding hydrochloride salt immediately after reduction on its own.

12 Claims, No Drawings

PROCESS FOR THE SYNTHESIS OF (±) 2-AMINO-N-[2,(2,5-DIMETHOXY PHENYL)-2-HYDROXYETHYL] ACETAMIDE MONOHYDROCHLORIDE

This application is a 371 of PCT/IN02/00170, filed Aug. 21, 2002.

TECHNICAL FIELD OF THE INVENTION (±)2-Amino-N-[2-(2,5-dimethoxy phenyl)-2-hydroxyethyl]acetamide mono hydrochloride known as midodrine hydrochloride has been known for its efficacy as a cardio vascular drug due to its long lasting blood pressure increasing effect.

BACKGROUND OF THE INVENTION

Of the several reported prior art for the synthesis of Midodrine hydrochloride, German patent specification DE 2523735 describes the use of substituted acetophenone as the starting material which is converted into the azido intermediate and then to the title compound. German patent specification DE 2506110 uses the amino alcohol intermediate as the starting material and uses the same reaction sequence disclosed in German patent DE 2523735 with the reduction of the azido group to the amino group in the final step using sodium borohydride or lithium aluminum hydride with additives and catalysts. In these prior art synthetic processes, the first stage intermediate is obtained from disubstituted acetophenones through bromination, azidation and reduction with hazardous reducing agents such as lithium aluminium hydride. Further, the hitherto known processes for the synthesis of midodrine hydrochloride do not result in good yields. Yet another drawback of the existing processes is that they are not reproducible or consistent on larger scales with respect to selectivity, yield and purity.

DISCLOSURE OF THE INVENTION

The objective of this invention is to synthesise (±)2-amino-N-[2-(2,5-dimethoxy phenyl)-2-hydroxyethyl]acetamide monohydrochloride (I) using cost effective reagents, under easy operating conditions, in good yields and high purity. The process according to this invention results in a consistent quality product in reproducible yields.

The reaction sequence of the process according to this invention is shown hereunder.

Step (a)

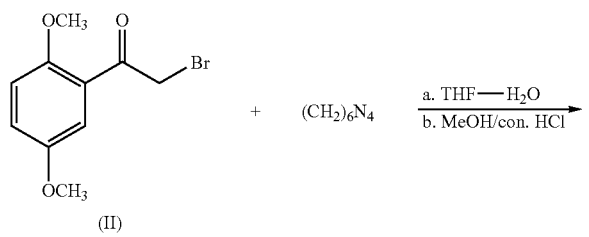

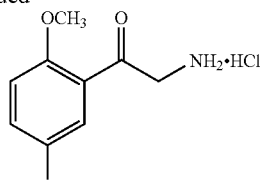

Step (b)

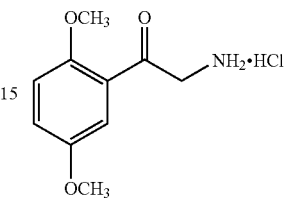

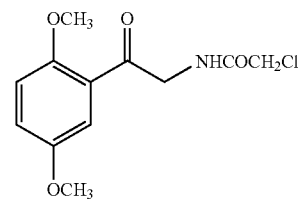

Step (c)

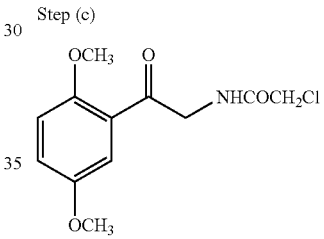

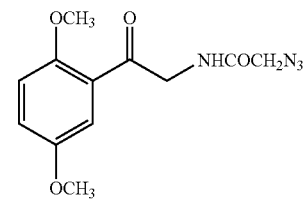

Step (d)

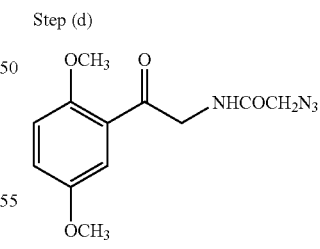

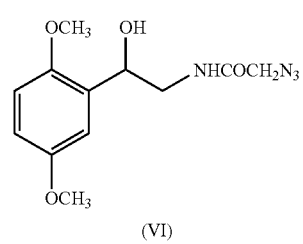

Step (e)

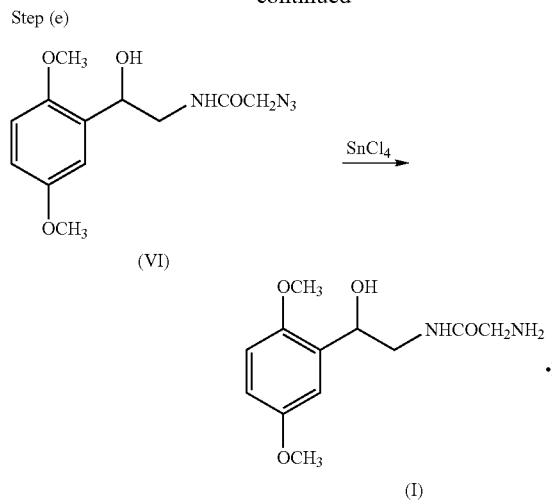

The aminomethanone intermediate of the formula III shown in the reaction scheme is prepared by reacting 1-(2,5-dimethoxy phenyl)-2-bromoethanone of the formula II with hexamethylenetetramine in tetrahydrofuran doped with water. This novel step of carrying out the reaction in a medium containing tetrahydrofuran and water enhances the speed of the reaction considerably while producing better yield. The volume of the solvent system is not critical but aids uniform agitation of the reactants. It is observed that the reaction is completed within 30 minutes whereas use of other solvent systems takes considerably longer periods of about 24 hours for complete complex formation. It has also been noticed that addition of sufficient water to the reaction mixture for effective stirring avoids or minimizes the production of polymeric byproducts. The product is digested with methanol and concentrated HCl as shown in step (a) in the reaction scheme. The resulting intermediate compound of formula III is washed with acetone and is found to have 99% purity.

Intermediate compound of formula IV is prepared by acylating 1-(2',5'-dimethoxy phenyl)-2-amino ethanone of formula III using chloroacetyl chloride and sodium acetate in the presence of acetone-water mixture. Use of acetone water mixture in carrying out the reaction is found to give better yield with easy work up process. This reaction is shown in step (b) in the reaction scheme.

Reaction scheme shown in step (c) is for the preparation of the intermediate compound of formula V from the compound of formula IV obtained in step (b) by nucleophilic azidation using sodium azide. This reaction is carried out in acetone as against the acetone water mixture used in prior art disclosures. It has been observed that presence of water leads to lower yields due to side reactions.

The compound of formula V prepared by step (c) is converted into (±)2-amino-N-[2-(2,5-dimethoxy phenyl)-2-hydroxyethyl]acetamide mono hydrochloride of formula I by reducing the carbonyl group selectively with sodium borohydride followed by reduction of the azide group with stannous chloride. There reactions are shown in step (d) and (e) in the reaction scheme. Prior art disclosed herein before follows simultaneous reduction of both the keto and azide groups in tetrahydrofuran using lithium aluminum hydride or sodium borohydride with 5% Palladium impregnated on carbon in methanol. Prior art methods suffer from disadvantages like difficulty in product isolation, product selectivity, and reproducibility on yields. The product conversion is very low with low purity. It has been found that by selectively reducing the compound of formula V under mild reaction conditions, using stannous chloride which has so far not been adopted and yet readily available and relatively cheap, the title compound can be isolated directly with good yield. Improved yields are noticed when hydrochloric acid and acetone are added to the reaction mixture.

This invention, therefore, relates to a process for synthesising (±)2-amino-N-[2-(2,5-dimethoxyphenyl)-2-hydroxyethyl]acetamide mono hydrochloride which comprises the steps of:

(a) reacting 1-(2,5-dimethoxy phenyl)-2-bromo ethanone with hexamine in tetrahydrofuran-water solvent system to produce 1-(2',5'-dimethoxyphenyl)-2-aminoethanone;

(b) acylating said 1-(2',5'-dimethoxy phenyl)-2-amino ethanone with haloacetylchloride and sodium acetate in acetone-water solvent medium to produce 2-chloro-N-(β-oxo-2,5-dimethoxyphenyl)acetamide;

(c) subjecting said acetamide obtained in step (b) to nucleophilic azidation with sodium azide in acetone medium;

(d) subjecting said 2-Azido-N-(β-oxo-2,5,dimethoxyphenethyl)acetamide to selective reduction of the carbonyl group by treating with sodium borohydride and;

(e) subsequently reducing the azide group with stannous chloride to obtain 2-amino-N-[2-(2,5-dimethoxy phenyl)-2-hydroxy ethyl acetamide which is converted into the corresponding monohydrochloride by treating with concentrated hydrochloric acid and recovered from the reaction mixture in a known manner.

BEST METHOD OF CARRYING OUT THE INVENTION

The following example describes the invention by way of illustration and is not included to limit the scope of the invention in any manner.

Step (a): Preparation of 1-(2',5'-dimethoxyphenyl)ethanone amine hydrochloride.

Quarternization:

In a four-neck round bottomed flask 500 gm of (1.93 mole) of 1-(2,5,-dimethoxyphenyl)-2-bromoethanone is added. 7500 ml of tetrahydrofuran is added to dissolve the solid. The agitator is switched on and solid gets dissolved immediately. 75 ml of water added into the flask under agitation. 270 gm of hexamine (1.93 mole) is added through powdered funnel. Immediately after the addition of hexamine thick precipitation is observed. Agitation is continued for 2 hours at ambient temperature. The resulting white precipitate is filtered under vacuum and the cake is washed with THF.

Conversion to Aminehydrochloride:

780 gms of solid obtained according to example (a) is taken into a round bottomed flask. 15600 ml of methanol is added and agitation is initiated. 1560 ml of concentrated HCl is added into the flask and agitation is continued. The mass is heated to reflux and maintained for 1 hr. The mass is evaporated to dry and cooled down. Acetone is added to this and stirred for 10 minutes, filtered, washed with acetone and dried under vacuum. The yield was 85%.

Step (b): Preparation of 2-Chloro-N-(β-oxo-2,5-Dimethoxy phenethyl)acetamide.

In a four neck round bottomed flask, 1500 ml of acetone is charged. 240 gm of 1(2',5'-dimethoxyphenyl)ethanone amine hydrochloride prepared according to step (a) is added under stirring. 500 ml of water is charged into the flask under stirring. The reaction mass is cooled down to 0° C. under stirring. 330 gm of sodium acetate is added till a pH of 5 is obtained. 77 gm of chloro acetyl chloride is added slowly over a period of 30 minutes while maintaining the temperature of 0° C. After addition is completed the reaction mass is stirred for 30 minutes. Agitation is stopped and the bottom aqueous layer is separated. The organic layer is concentrated and water is added. The precipitated material is filtered and dried. The solid is crystallized from methanol.

The following physical properties are measured. Melting point: 140–142° C.

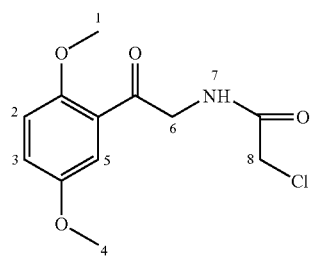

$^1$H-NMR(CDCl$_3$): δ(ppm): 3.9 (3H, s, H-1), 3.7 (3H, s, H-4), 4.1 (2H, s, H-8), 4.7 (2H, d, H-6), 6.9 (1H, d, H-2), 7.1 (1H, dd, H-3), 7.5 (1H, d, H-5), 7.7 (1H, s, H-7).

Step (c): Preparation of 2-Azido-N-(β-oxo-2,5-dimethoxy phenehyl)acetamide.

In a four neck round bottomed flask, 45 gm (0.165 mole) of 2-Chloro-N-(β-oxo-2,5-Dimethoxy phenethyl)-acetamide prepared according to step (b), 27 g (0.415 mole) sodium azide and 8.3 g (0.049 mole) potassium iodide and 900 ml of acetone is charged. The solution is refluxed at 60° C. for 5 hours. After completion of the reaction the reaction mass cooled and filtered to remove inorganics. Acetone is distilled off under atmospheric pressure. Water is added and the resulting yellow lumps are filtered. (Yield: 91%). The solid is recrystallized from methanol. The following physical properties are measured.

Melting point: 104–106° C.

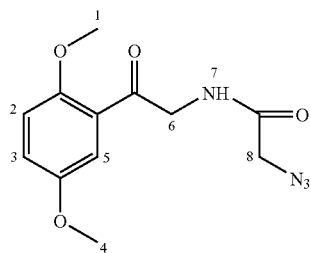

$^1$H-NMR(CDCl$_3$): δ(ppm): 3.9 (3H, s, H-1), 3.7 (3H, s, H-4), 4.0 (2H, s, H-8), 4.7 (2H, d, H-6), 6.9 (1H, d, H-2), 7.1 (1H, m, H-3), 7.4 (1H, s, H-7), 7.5 (1H, d, H-5).

Step (d): Preparation of 2-Azido-N-(β-hydroxy-2,5-dimethoxy phenethyl)acetamide.

In a four neck round bottomed flask 32.4 gm (0.11 mole) of 2-azido-N-(β-Oxo-2,5-dimethoxy phenehyl)-acetamide is prepared according to the step (c) and 260 ml methanol is charged and cooled to 0° C. To this 3.24 gm (0.08 mole) sodium boro hydride is added slowly over a period. After completion of the addition, the reaction mass temperature is raised to 10° C. After completion of the reaction, 10 ml of acetic acid is added. Methanol is stripped off under reduced pressure and the residue obtained is extracted with methylene dichloride. Organic layer is washed with water and methylene dichloride is distilled off. The yield was 95%.

Step (e): Preparation of ±1-(2',5'-dimethoxyphenyl)-2-glycineamido-ethanol-(1)-HCl.

In a four neck round bottomed flask 95 ml methanol and 27.5 gm (0.122 mole) stannous chloride are charged. The mixture is agitated and cooled down to 25° C. 19.0 gm (0.067 mole) of 2-Azido-N-(β-hydroxy-2,5-dimethoxy phenethyl)-acetamide prepared according to step (d) and 30 ml methanol are added over a period of 30 minutes. The reaction mass maintained at ambient temperature for 1 hr. Concentrated hydrochloric acid 57 ml is added and agitated for 15 minutes. The precipitate obtained is filtered and washed with acetone. The yield was 85% and HPLC purity was 99.7%.

The following physical properties are measured on the product.

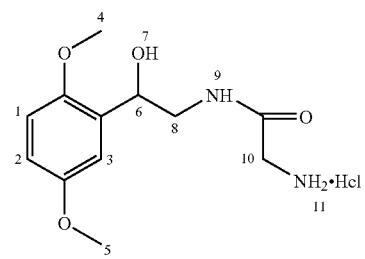

M.Pt: 200–202° C.
$^1$H-NMR(CDCl$_3$): δ(ppm): 3.39 (1H, dd, 8Ha), 3.55 (1H, dd, 8Hb), 3.66 (2H, two closely spaced doublet, 10H), 3.73 (H, s, 4-OCH2), 3.78 (3H, s, 5-OCH3), 5.09 (1H, q, H-6), 6.8 (1H, 0-m double doublet, 2-H), 6.88 (1H, 0-d, 1-H), 7.05 (1H, m-d, 2-H).

The invention claimed is:

1. A process for synthesising (±)2-amino-N-[2-(2,5-dimethoxyphenyl)-2-hydroxyethyl]acetamide monohydrochloride which comprises the steps of:
   (a) reacting 1-(2,5-dimethoxyphenyl)-2-bromoethanone with hexamine in tetrahydrofuran water solvent system to produce 1-(2',5'-dimethoxyphenyl)-2-amino ethanone;
   (b) acylating said 1-(2',5'-dimethoxyphenyl)-2-aminoethanone with haloacetylchloride and sodium acetate in acetone water solvent medium to produce 2-chloro-N-(β-oxo-2,5-dimethoxyphenyl)acetamide;
   (c) subjecting said acetamide obtained in step (b) to nucleophilic azidation with sodium azide in acetone medium;
   (d) subjecting said 2-azido-N-(β-oxo-2,5,-dimethoxyphenyl)acetamide to selective reduction of the carbonyl group by treating with sodium borohydride and subsequently reducing the azide group with stannous chloride to obtain (±)2-amino-N-[-2-(2,5-dimethoxyphenyl)-2-hydroxyethyl]acetamide which is converted into the corresponding monohydrochloride by treatment with concentrated hydrochloric acid and recovered from the reaction mixture in a known manner.

2. The process as claimed in claim 1 wherein the haloacetyl chloride used in step (b) is chloroacetyl chloride and the reaction is carried out at 0° C.

3. The process as claimed in claim 1 wherein potassium iodide is added to the reaction mixture in step (c) and the reaction mixture is refluxed at a temperature of about 60° C.

4. The process as claimed in claim 1 wherein the selective reduction in step (d) is carried out in a protic solvent.

5. The process as claimed in claim 1 wherein conversion to monohydrochloride is effected in situ by adding concentrated hydrochloric acid in the presence of an aprotic solvent.

6. (±)2-Amino-N-[2-(2,5-dimethoxyphenyl)-2-hydroxyethyl]acetamide whenever prepared by a process as claimed in claim 1.

7. The process as claimed in claim 2 wherein potassium iodide is added to the reaction mixture in step (c) and the reaction mixture is refluxed at a temperature of about 60° C.

8. The process as claimed in claim 2 wherein the selective reduction in step (d) is carried out in a protic solvent.

9. The process as claimed in claim 3, wherein the selective reduction in step (d) is carried out in a protic solvent.

10. The process of claim 1, wherein 2-Azido-N-(β-hydroxy-2,5-dimethoxy phenethyl)-acetamide is obtained after selective reduction of the carbonyl group.

11. The process of claim 1, wherein (±)2-amino-N-[-2-(2,5-dimethoxyphenyl)-2-hydroxyethyl]acetamide is obtained after selective reduction of 2-Azido-N-(β-hydroxy-2,5-dimethoxy phenethyl)-acetamide with stannous chloride.

12. The process of claim 11, further comprising adding methanol to the reaction mixture containing 2-Azido-N-(β-hydroxy-2,5-dimethoxy phenethyl)-acetamide and then adding concentrated hydrochloric acid to obtain (±)2-amino-N-[-2-(2,5-dimethoxyphenyl)-2-hydroxyethyl]acetamide hydrochloride salt.

* * * * *